US012626822B2

(12) United States Patent
Fabbri et al.

(10) Patent No.: US 12,626,822 B2
(45) Date of Patent: May 12, 2026

(54) DEEP LEARNING FOR AUTOMATED SMILE DESIGN

(71) Applicant: Solventum Intellectual Properties Company, Maplewood, MN (US)

(72) Inventors: Cameron M. Fabbri, St. Paul, MN (US); Wenbo Dong, Lakeville, MN (US); James L. Graham, II, Woodbury, MN (US); Cody J. Olson, Ham Lake, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 128 days.

(21) Appl. No.: 18/291,821

(22) PCT Filed: Aug. 5, 2022

(86) PCT No.: PCT/IB2022/057323
§ 371 (c)(1),
(2) Date: Jan. 24, 2024

(87) PCT Pub. No.: WO2023/017390
PCT Pub. Date: Feb. 16, 2023

(65) Prior Publication Data
US 2024/0347210 A1 Oct. 17, 2024

Related U.S. Application Data

(60) Provisional application No. 63/231,823, filed on Aug. 11, 2021.

(51) Int. Cl.
*G16H 50/50* (2018.01)
*G06T 5/60* (2024.01)
(Continued)

(52) U.S. Cl.
CPC .............. *G16H 50/50* (2018.01); *G06T 5/60* (2024.01); *G06T 5/77* (2024.01); *G06T 11/00* (2013.01);
(Continued)

(58) Field of Classification Search
CPC .. G16H 50/50; G06T 5/60; G06T 5/77; G06T 11/00; G06T 2207/30036; G06T 2210/41;
(Continued)

(56) References Cited

U.S. PATENT DOCUMENTS

| | | | |
|---|---|---|---|
| 7,605,817 B2 | 10/2009 | Zhang | |
| 7,956,862 B2 | 6/2011 | Zhang | |

(Continued)

FOREIGN PATENT DOCUMENTS

| | | | |
|---|---|---|---|
| KR | 20200046843 A | 5/2020 | |
| WO | 2019213129 A1 | 11/2019 | |

(Continued)

OTHER PUBLICATIONS

Wikipedia: "Generative adversarial network—Wikipedia", Aug. 8, 2021 (Aug. 8, 2021), XP093274881,Retrieved from the Internet: URL:https://en.wikipedia.org/w/index.php?t itle=Generative_ adversarial_network&oldid=1037818223 [retrieved on May 6, 2025].
(Continued)

*Primary Examiner* — Maurice L. McDowell, Jr.

(57) ABSTRACT

A method for displaying teeth after planned orthodontic treatment in order to show persons how their smiles will look after the treatment. The method includes receiving a digital 3D model of teeth or rendered images of teeth, and an image of a person such as a digital photo. The method uses a generator network to produce a generated image of the person showing teeth of the person, the person's smile, after the planned orthodontic treatment. The method uses a discriminator network processing input images, generated
(Continued)

images, and real images to train the generator network through deep learning models to product a photo-realistic image of the person after the planned treatment.

20 Claims, 4 Drawing Sheets

(51) Int. Cl.

| | |
|---|---|
| *G06T 5/77* | (2024.01) |
| *G06T 11/00* | (2006.01) |
| *G06V 10/40* | (2022.01) |
| *G06V 10/764* | (2022.01) |
| *G06V 10/774* | (2022.01) |
| *G06V 10/82* | (2022.01) |

(52) U.S. Cl.
CPC ............ *G06V 10/40* (2022.01); *G06V 10/764* (2022.01); *G06V 10/774* (2022.01); *G06V 10/82* (2022.01); *G06T 2207/30036* (2013.01); *G06T 2210/41* (2013.01)

(58) Field of Classification Search
CPC ...... G06T 17/00; G06V 10/40; G06V 10/764; G06V 10/774; G06V 10/82; G06N 3/045; G06N 3/0475; G06N 3/094; A61C 7/00; A61C 9/00
See application file for complete search history.

(56) References Cited

U.S. PATENT DOCUMENTS

| | | | | |
|---|---|---|---|---|
| 2018/0028294 A1* | 2/2018 | Azernikov | ........ | G06F 18/24143 |
| 2019/0350680 A1* | 11/2019 | Chekh | .................... | A61C 7/002 |
| 2020/0229900 A1 | 7/2020 | Cunliffe | | |
| 2020/0342586 A1* | 10/2020 | Kumar | ..................... | G06T 7/13 |
| 2020/0360109 A1* | 11/2020 | Gao | ..................... | A61C 9/0053 |
| 2022/0084653 A1* | 3/2022 | Yang | ......................... | G06T 7/73 |

FOREIGN PATENT DOCUMENTS

| | | |
|---|---|---|
| WO | 2020202009 A1 | 10/2020 |
| WO | 2021108016 W | 6/2021 |

OTHER PUBLICATIONS

International Search Report for PCT/IB2022/057323 mailed on Nov. 18, 2022, 4 pages.
Realistic high-resolution lateral cephalometric radiography generated by progressive growing generative adversarial network and quality evaluations, Dated: Jun. 15, 2021.

\* cited by examiner

DEEP LEARNING FOR AUTOMATED SMILE DESIGN

CROSS-REFERENCE TO RELATED APPLICATIONS

This Application is a national stage filing under 35 U.S.C. § 371 of International Application No. PCT/IB2022/057323, filed 5 Aug. 2022, which claims the benefit of Provisional U.S. Patent Application No. 63/231,823, filed 11 Aug. 2021, the entire disclosure of each of which is incorporated herein by reference.

BACKGROUND

Orthodontic clear tray aligners allow patients to receive high quality, customizable treatment options. A potential patient may browse past clinical cases if they are considering getting treatment. A high-level overview of one pipeline is as follows: a potential patient will arrive at the doctor's office: the doctor will take a scan of their teeth, extracting a three-dimensional (3D) mesh; and this 3D mesh is processed by an algorithm to produce a mesh of the patient's teeth in their final alignment.

A common question from patients is, "what would my new smile look like?" While they have the ability to view previous clinical trials and even the ability to view the 3D mesh of their newly aligned teeth, neither option provides the patient with a true feel of what their teeth and smile may look like after orthodontic treatment. Because of this, potential patients may not be fully committed to receiving treatment.

SUMMARY

A method for displaying teeth after planned orthodontic treatment includes receiving a digital 3D model of teeth or rendered images of teeth, and an image of a person. The method uses a generator network to produce a generated image of the person showing teeth of the person after the planned orthodontic treatment. The method uses a discriminator network processing input images, generated images, and real images to train the generator network.

DETAILED DESCRIPTION

Embodiments include an automated system to generate an image of a potential person's smile showing post-treatment aligner results, before treatment has begun. The system utilizes data including a person's image as well as their corresponding 3D scan in order to learn how to generate a photo-realistic image. Though the system is trained to generate a person's smile from their pre-treatment scan, the scan can be swapped out with a post-treatment scan in order to give the person the ability to view potential post-treatment results. Alternatively or in addition, the system can be used to show persons their appearance after each stage, treatment, or selected stages of treatment.

The ability for a person to view a post-treatment photo of themselves smiling, before any treatment has begun, may give them confidence moving forward with the treatment process, as well as help convince those who may be uncertain. Additionally, the person would be able to provide feedback to the doctor or practitioner if any aesthetic changes are requested, and the doctor or practitioner can modify the alignment of the mesh to meet the person's needs.

Figure 1:
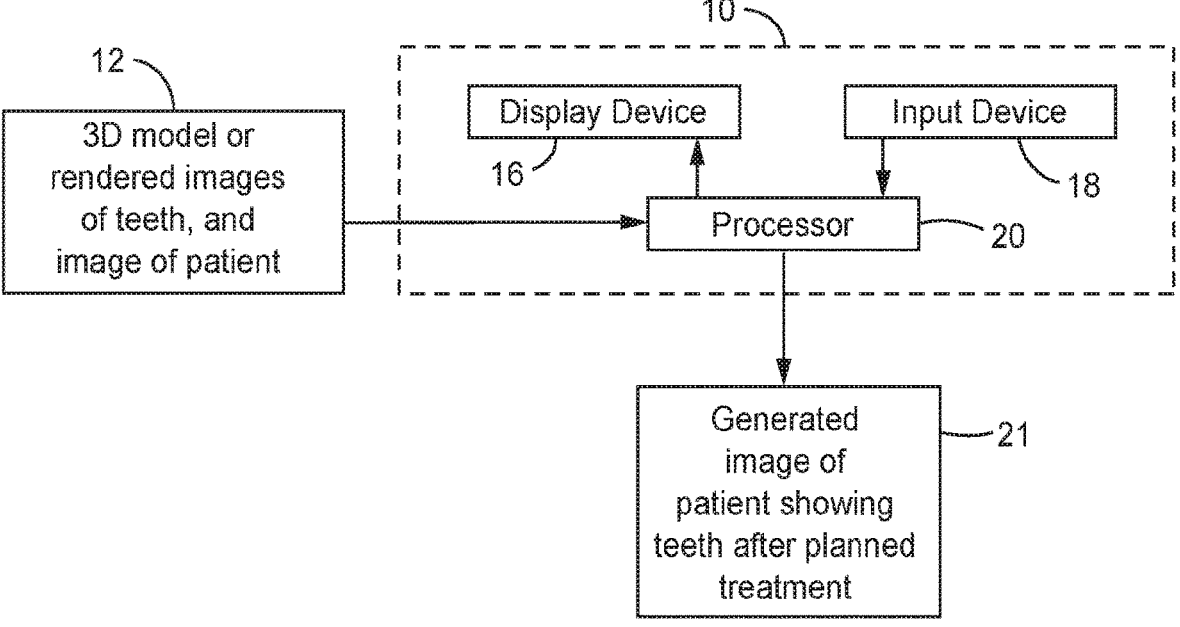
FIG. 1 is a diagram of a system for generating an image of a person's smile showing post-treatment results.

FIG. 1 is a diagram of a system 10 for generating an image of a person's smile showing post-treatment results (21). System 10 includes a processor 20 receiving a digital 3D model (mesh) or rendered images of teeth and an image (e.g., digital photo) of the corresponding person (12). The digital 3D model can be generated from, for example, intra-oral 3D scans or scans of impressions of teeth. System 10 can also include an electronic display device 16, such as a liquid crystal display (LCD) device, and an input device 18 for receiving user commands or other information. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth and gingiva. System 10 can be implemented with, for example, a desktop, notebook, or tablet computer.

The system is built upon generative machine or deep learning models known as Generative Adversarial Networks (GANs). This class of algorithms contains a pair of differentiable functions, often deep neural networks, whose goal is to learn an unknown data distribution. The first function, known as the generator, produces a data sample given some input (e.g., random noise, conditional class label, or others). The generator and feature extracting network also receive the pixel-wise difference between the generated and ground truth image in the form of a loss function. The second function, known as the discriminator, attempts to classify the "fake" data generated by the generator from the "real" data coming from the true data distribution. As the generator continuously tries to fool the discriminator into classifying data as "real," the generated data becomes more realistic.

The system uses a conditional GAN (cGAN), where the generator is conditioned on either a two-dimensional (2D) rendered image of the person's scanned teeth, or the 3D mesh model of their teeth, along with an image of the person smiling with their teeth blocked out. The generator (see FIG. 2), represented as a Convolutional Neural Network (CNN), aims to use the conditional information given from their scan in order to inpaint the missing data for their smile.

Figure 2:
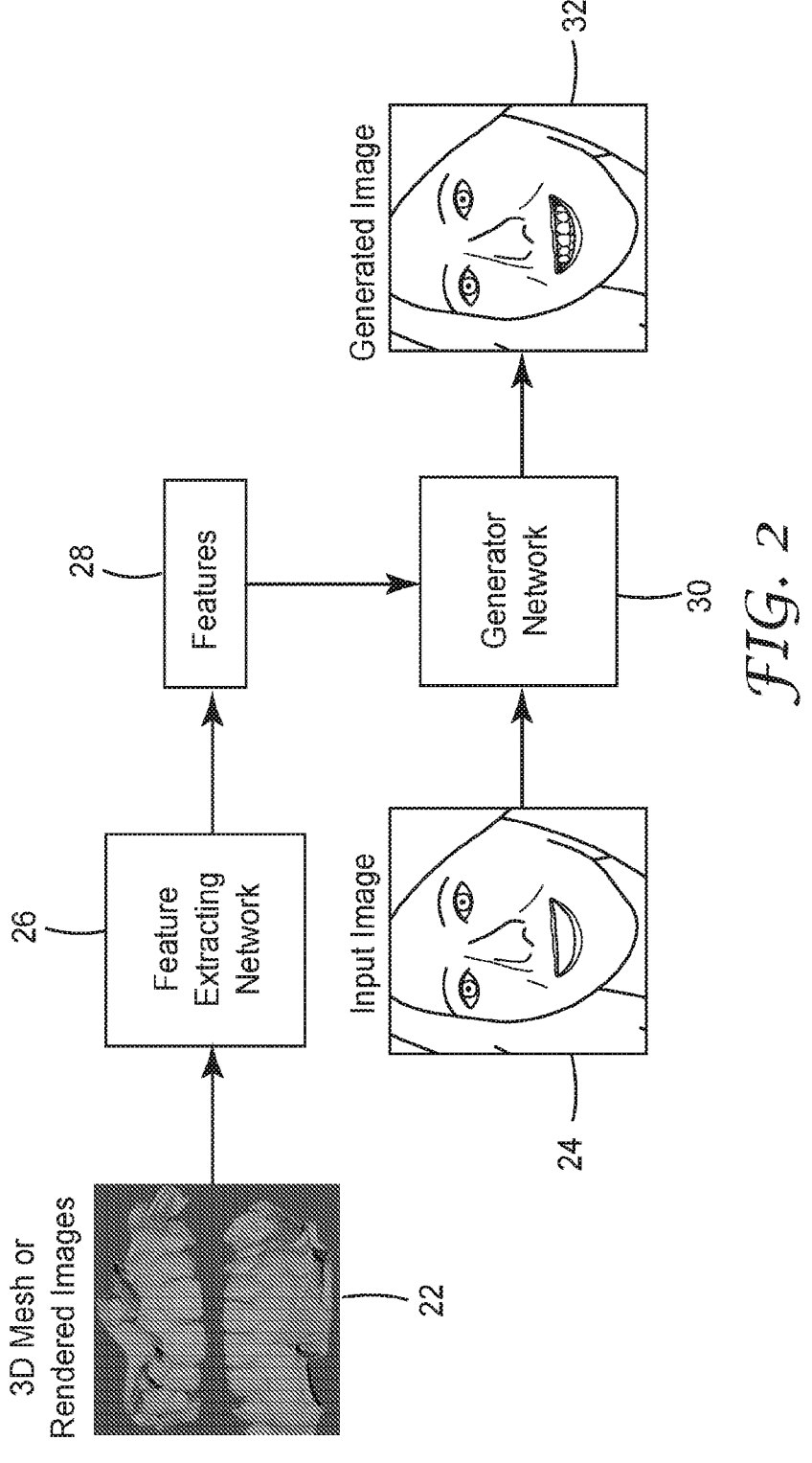
FIG. 2 is a diagram of a generator network for the system.

As shown in FIG. 2, a generator network 30 receives a 3D mesh or rendered images of teeth (22) via a feature extracting network 26 providing features 28. Feature extracting network 26 can be implemented with, for example, an inference engine to provide the features in a less noisy output mesh or rendered image. Generator network 30 also receives an image (e.g., digital photo) of the person's face (24). Generator network 30 then generates an image of that person smiling (32) with the respective teeth model that it was given, allowing persons to view their smile with any number of different styles of teeth. Specifically, the system can target viewing the post-treatment smile as a use case.

Figure 3:
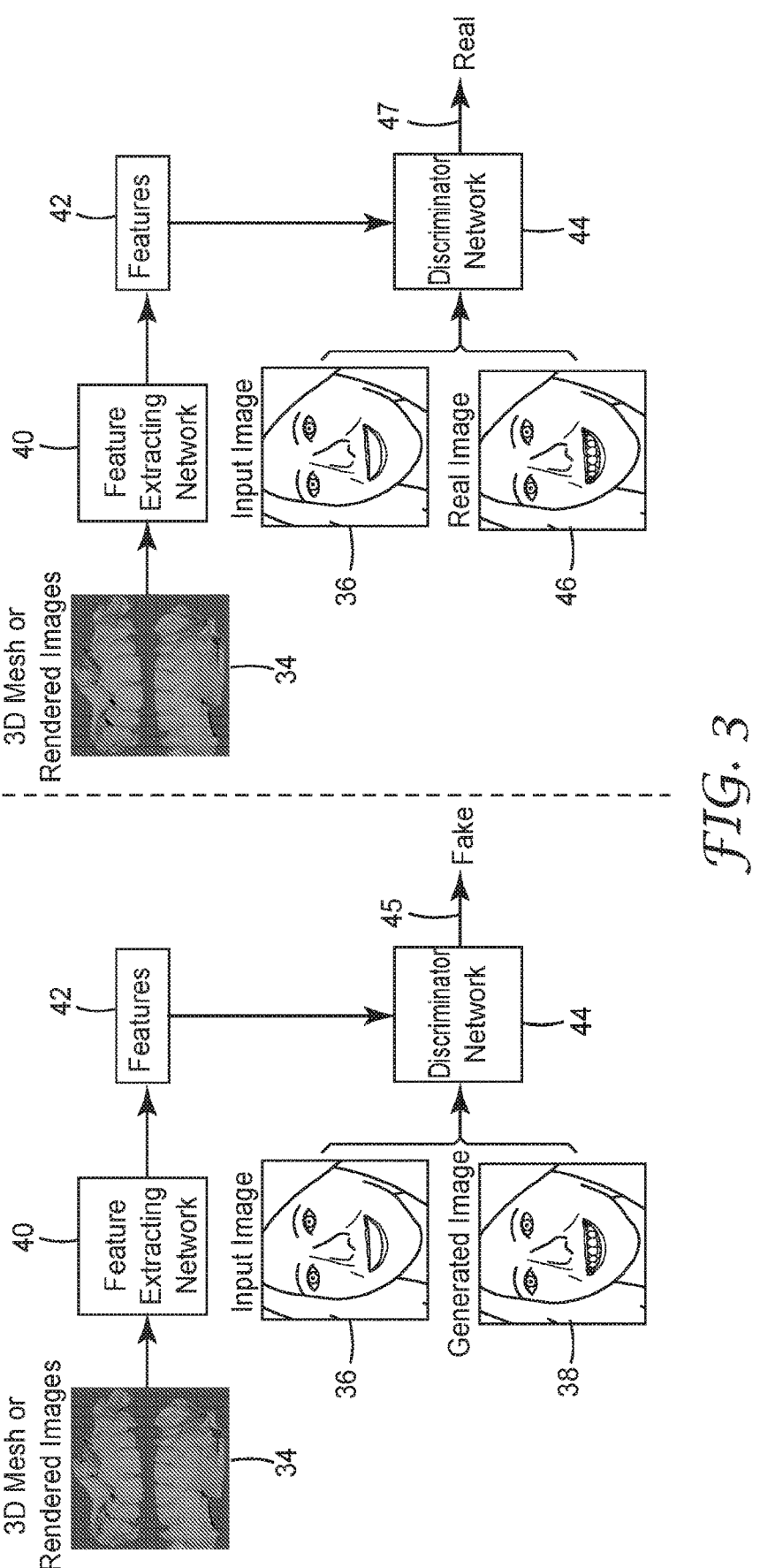
FIG. 3 is a diagram of a discriminator network for the system.

The discriminator, also represented as a CNN, has two training steps. As shown in FIG. 3, a discriminator network 44 receives a 3D mesh or rendered images of teeth (34) via a feature extracting network 40 providing features 42. Feature extracting network 40 can be implemented with, for example, an inference engine to provide the features in a less noisy output mesh or rendered image. In the first step, discriminator network 44 is given the image (e.g., digital photo) of the person with their mouth blocked (36), a real image of the person without their mouth blocked (46), and features (42) of person's scan extracted from another neural network. In this case, discriminator network 44 should classify the triplet of data as "real" (47), as the photo of the person comes from the real dataset. In the second step discriminator network 44 is again given the image (e.g., digital photo) of the person with their mouth blocked (36), features (42) of person's scan extracted from another neural network, but this time a generated image (38) from the generator. In this case, discriminator network 44 should classify the triplet of data as "fake" (45). The generator and discriminator are trained simultaneously, improving upon each other.

The images of the person smiling with their teeth blocked out can be generated by finding features of the smile in the images (e.g., corners of the mouth), extracting the bounds of those features, and whiting out those features.

The generator network, discriminator network, and feature extracting network can be implemented in, for example, software or firmware modules for execution by a processor such as processor 20. The generated images can be displayed on, for example, display device 16.

The dataset for the following experiment consisted of ~5,000 patients. Each patient has a front facing photo of themselves smiling, as well as a scan of their teeth. For this experiment, we used a 2D render for the scan as the conditional information.

Figure 4:
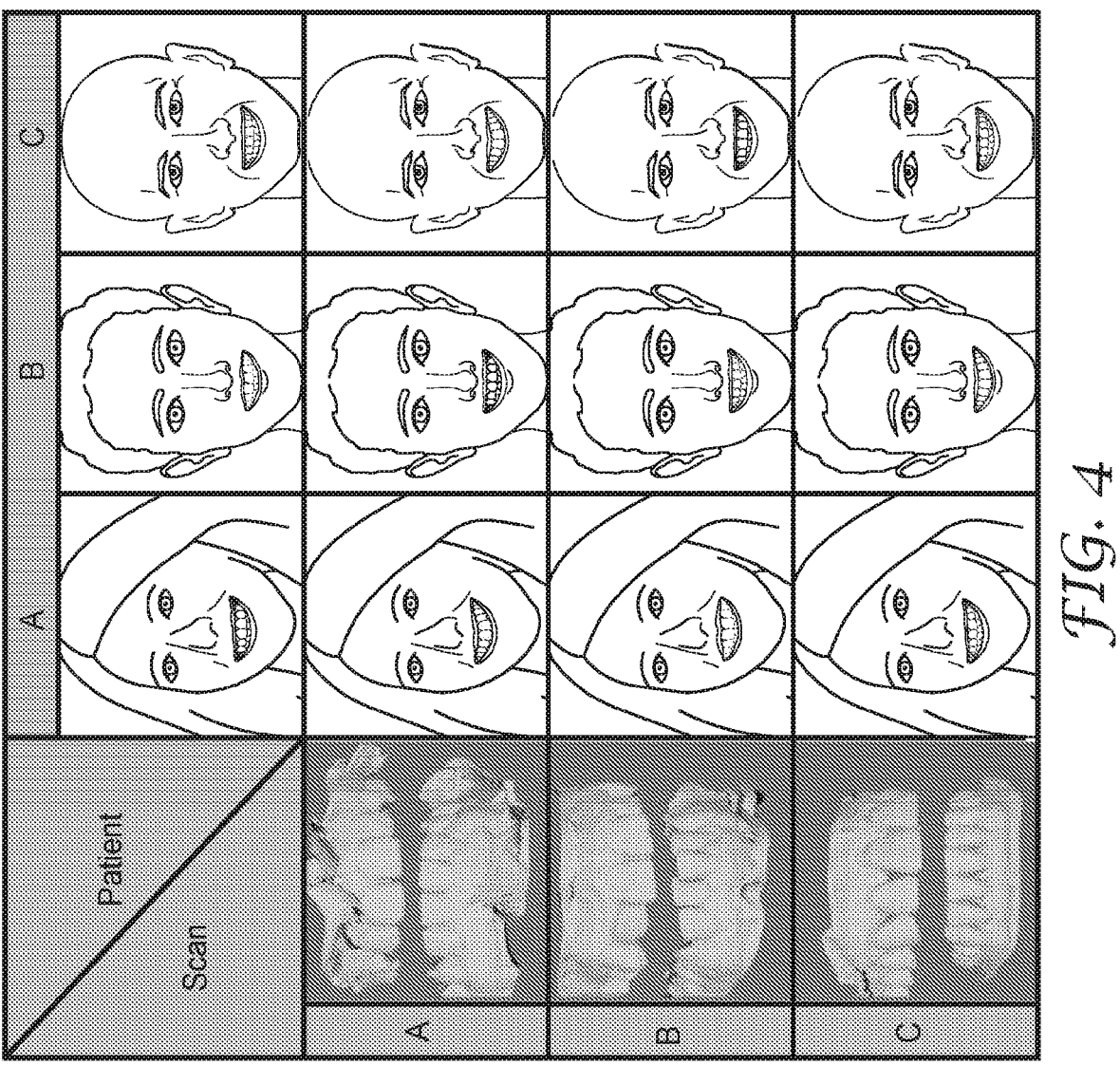
FIG. 4 shows some results after training the system.

FIG. 4 shows results after training the system. Each column contains a different patient, whereas each row contains the matching patient's scan (e.g., the patient in column A matches their scan in row A). In practice, the system would work as follows. A potential patient would arrive at the doctor and receive a scan of their teeth. This scan would be processed by a staging algorithm in order to place the teeth in their final alignment or in an intermediate stage of treatment. Staging algorithms to generate intermediate and final stages or setups are described in, for example, US Patent Application Publication No. 2020/0229900 and PCT Application Publication No. 2020/202009. Using the generator network, this scan would then be swapped with the patient's pre-treatment scan in order to generate a photo of them with post-treatment results. Swapping the scans can include filling in the blocked out mouth of the person from the input image.

In order to test the viability of this, we swapped the scans of different patients, then generated their corresponding photo. For example, Column A in FIG. 4 shows generated photos of Patient A with their own scan (Row A), as well as with scans from Patients B and C (Rows B and C).

In FIGS. 2-4, line drawings are used to represent the persons and their smiles. An implementation would typically use actual photos, real and generated, as described above.

The invention claimed is:

1. A computer-implemented method for displaying teeth after planned orthodontic treatment, comprising:

receiving, by a computing device, a digital three-dimension (3D) model of teeth or rendered images of teeth, and an image of a person;

processing, by a generator network implemented on the computing device, the digital 3D model and the image of the person to produce a photo-realistic generated image of the person showing teeth of the person after the planned orthodontic treatment of the teeth;

training the generator network using adversarial learning by a discriminator network that processes input images, generated images, and real images to improve image realism; and displaying, on a graphical user interface of the computer device, the generated image of the person showing the results of the planned orthodontic treatment.

2. The method of claim 1, further comprising receiving a final alignment or stage of the teeth after the planned orthodontic treatment.

3. The method of claim 2, further comprising blocking out teeth of the person in the received image.

4. The method of claim 3, wherein using the generator network comprises filling in the blocked out teeth in the received image with the final alignment or stage of the teeth.

5. The method of claim 1, further comprising using a feature extracting network to extract features from the digital 3D model of teeth or rendered images of teeth for the generator network.

6. The method of claim 1, further comprising using a feature extracting network to extract features from the digital 3D model of teeth or rendered images of teeth for the discriminator network.

7. The method of claim 1, wherein the image comprises a digital photo.

8. The method of claim 1, wherein when the discriminator network is provided with real images, the discriminator network classifies the input images as real in order to train the generator network.

9. The method of claim 1, wherein when the discriminator network is provided with generated images, the discriminator network classifies the input images as fake in order to train the generator network.

10. The method of claim 1, wherein the planned orthodontic treatment comprises a final stage or setup.

11. The method of claim 1, wherein the planned orthodontic treatment comprises an intermediate stage or setup.

12. A system for displaying teeth after planned orthodontic treatment, comprising a processor configured to:

receive, by the system, a digital three-dimension (3D) model of teeth or rendered images of teeth, and an image of a person;

process, by a generator network implemented on the computing device, the digital 3D model and the image of the person to produce a photo-realistic generated image of the person showing teeth of the person after the planned orthodontic treatment of the teeth;

train the generator network using adversarial learning by a discriminator network that processes input images, generated images, and real images to improve image realism; and display, on a graphical user interface of the system, the generated image of the person showing the results of the planned orthodontic treatment.

13. The system of claim 12, wherein the processor is further configured to receive a final alignment or stage of the teeth after the planned orthodontic treatment.

14. The system of claim 13, wherein the processor is further configured to block out teeth of the person in the received image.

15. The system of claim 14, wherein to use the generator network, the processor is configured to fill in the blocked out teeth in the received image with the final alignment or stage of the teeth.

16. The system of claim 12, wherein the processor is further configured to use a feature extracting network to extract features from the digital 3D model of teeth or rendered images of teeth for the generator network.

17. The system of claim 12, wherein the processor is further configured to use a feature extracting network to extract features from the digital 3D model of teeth or rendered images of teeth for the discriminator network.

18. The system of claim 12, wherein the image comprises a digital photo.

19. The system of claim 12, wherein when the discriminator network is provided with real images, the discriminator network classifies the input images as real in order to train the generator network.

20. The system of claim 12, wherein when the discriminator network is provided with generated images, the discriminator network classifies the input images as fake in order to train the generator network.

\* \* \* \* \*